(12) United States Patent
Ansmann et al.

(10) Patent No.: US 6,790,996 B2
(45) Date of Patent: Sep. 14, 2004

(54) SUPPORTED COBALT CATALYSTS FOR NITRILE HYDROGENATIONS

(75) Inventors: Andreas Ansmann, Wiesloch (DE); Christoph Benisch, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/271,977

(22) Filed: Oct. 17, 2002

(65) Prior Publication Data

US 2003/0120115 A1 Jun. 26, 2003

(30) Foreign Application Priority Data

Oct. 23, 2001 (DE) .......................................... 101 52 135

(51) Int. Cl.$^7$ .......................... C07C 29/48; B01J 23/00
(52) U.S. Cl. ................. 564/491; 564/413; 564/415; 564/448; 564/487; 564/492; 564/493; 502/325
(58) Field of Search ................................ 564/413, 415, 564/448, 487, 491–493

(56) References Cited

U.S. PATENT DOCUMENTS

| | | | |
|---|---|---|---|
| 4,420,648 A | * 12/1983 | Carter et al. | 585/269 |
| 4,721,811 A | 1/1988 | Sherwin et al. | 564/491 |
| 5,132,427 A | 7/1992 | Koehler et al. | 546/246 |
| 5,574,189 A | * 11/1996 | Vedage et al. | 564/493 |
| 5,869,653 A | 2/1999 | Johnson | 540/531 |
| 6,005,145 A | 12/1999 | Cordier et al. | 564/490 |

FOREIGN PATENT DOCUMENTS

| | | |
|---|---|---|
| DE | 1 518 118 | 11/1969 |
| EP | 0 424 738 | 5/1991 |
| EP | 0 566 197 | 10/1993 |
| WO | WO 97/10052 | 3/1997 |

OTHER PUBLICATIONS

Database CAPLUS on STN, Acc. No. 2000:75595, Wang et al., Cuihua Xuebao (1999), 20(5), pp. 548–552 (abstract).*

* cited by examiner

*Primary Examiner*—Brian Davis
(74) *Attorney, Agent, or Firm*—Keil & Weinkauf

(57) ABSTRACT

The invention relates to a process for preparing primary amines by hydrogenating nitrites in the presence of a catalyst comprising cobalt and optionally, in addition, nickel and also at least one further doping metal on a particulate support material, the cobalt and, if present, the nickel having an average particle size of from 3 to 30 nm in the active catalyst. The invention further relates to the use of the catalyst in a process for preparing primary amines by hydrogenating nitrites.

25 Claims, No Drawings

SUPPORTED COBALT CATALYSTS FOR NITRILE HYDROGENATIONS

The invention relates to a process for preparing primary amines by hydrogenating nitriles in the presence of a supported catalyst comprising cobalt and optionally, in addition, nickel. The invention further relates to the use of this catalyst in a process for preparing primary amines by hydrogenating nitriles.

The hydrogenation of nitriles provides, depending on the reaction conditions and the catalyst used, primary, secondary or tertiary amines, although in general, a mixture of all three amine types is obtained. In the past, intensive research was carried out toward controlling selective hydrogenation to give one type of amine. The removal of secondary and tertiary amines from, for example, the desired primary amines requires additional apparatus and additional energy. It was found that improved selectivity to give primary amines may be achieved by adding ammonia to the reaction mixture. The hydrogenation of dinitriles suffers from the problem of condensation reactions which lead to cyclic products or oligomers.

Selectivity of nitrile hydrogenation is also influenced by the nature of the catalyst. The nature of the catalyst also influences the temperature necessary for the hydrogenation of the nitriles. For instance, in particular in the case of nitriles which are unstable under severe conditions such as high temperatures or in the case of hydrogenation of nitriles where, for example, a certain isomeric ratio is desired, hydrogenation at very low temperatures under protective conditions is desirable. According to the prior art, the most suitable catalysts for hydrogenating nitriles at very low temperatures and with high selectivity are Raney nickel and Raney cobalt.

For instance, U.S. Pat. No. 4,721,811 relates to a continuous process for preparing linear polyamines by hydrogenating polynitriles. The catalyst used is granular Raney cobalt which is obtainable by leaching of corresponding nuggets of the alloy.

U.S. Pat. No. 5,869,653 also relates to a process for catalytically hydrogenating nitriles. The catalyst used is a Raney cobalt catalyst and the hydrogenation takes place in the presence of catalytic quantities of lithium hydroxide and water.

However, the use of Raney catalysts and the preparation thereof brings disadvantages. For instance, Raney catalysts are pyrophoric, so they may only be transported, stored and introduced into the reactors under liquid or with the exclusion of air. The preparation of Raney catalysts is also very complicated, since a starting alloy first has to be prepared by melting, which then has to be leached using considerable quantities of concentrated bases. Afterwards, washing with water results in strongly basic waste water which, for ecological reasons, has to be worked up in a complicated manner or disposed of.

Accordingly, there is a great interest in replacing the Raney catalysts by other, less problematically handled catalysts.

A possibility is the use of supported catalysts. However, according to the prior art, these generally have low selectivities. However, supported catalysts are also known for which selectivity improvement by doping or by the use of cocatalysts is suggested.

For instance, EP-A 0 566 197 relates to a process for preparing primary amines by hydrogenating mono- and/or dinitriles using hydrogen in the presence of nickel and/or cobalt catalysts on a support material, preferably in combination with at least one solid cocatalyst which is insoluble in the reacton medium and the catalyst and/or cocatalyst are substantially nonacid. According to the examples, it was found that the addition of alkali metals or of alkaline earth metals results in a selectivity increase at an only slightly reduced activity. However, these reactions take place at 130 or 140° C., i.e. under conditions which are unsuitable for thermally labile nitriles.

The use of a cocatalyst leads to increased complication, in particular when alkali metals or alkaline earth metals are used.

EP-A 0 424 738 relates to a process for preparing linear triamino compounds by reacting 1,3,6-tricyanohexane over a catalyst comprising cobalt oxide and also an oxide of alkali metals, alkaline earth metals, rare earths or scandium or yttrium. The catalyst may be unsupported or supported. The catalyst has insufficient activity which is noticeable by low space-time yields and the severe hydrogenation conditions (in particular, pressure of 300 bar).

DE-A 1 518 118 relates to a process for hydrogenating nitriles which employs cobalt catalysts comprising magnesium oxide. These may be unsupported or supported catalysts. According to Example 1 of DE-A 1 518 118, the active catalysts used are those in which 55% of the cobalt is present as cobalt metal. According to the examples, hydrogenation is carried out at temperatures of from 100 to 140° C. Accordingly, this process is likewise unsuitable for hydrogenating thermally labile nitriles.

WO 97/10052 relates to a process for hydrogenating nitriles which employs hydrogenation catalysts comprising at least one divalent metal in partially reduced form (preferably Ni or Co) and at least one doping metal selected from the group consisting of Cr, Mo, Fe, Mn, Ti, V, Ga, In, Bi and rare earths in oxidic form. WO 97/10052 also relates to the catalysts themselves. The catalysts disclosed by WO 97/10052 are unsupported catalysts which consist predominantly of the active metal and are accordingly very expensive.

It is an object of the present invention to provide a process for preparing primary amines by hydrogenating nitriles which employs catalysts which are easy to handle and provide better value for money than unsupported catalysts, have high activities and selectivities for hydrogenating nitriles and are usable either as a powder in a suspension process or else as a shaped article in a fixed bed process. These catalysts shall also have high activity and selectivity toward primary amines even at low temperatures, so that the process is suitable for hydrogenating thermally labile nitriles.

We have found that this object is achieved by a process for preparing primary amines by hydrogenating nitriles in the presence of a catalyst comprising cobalt and optionally, in addition, nickel and also at least one further doping metal on a particulate support material.

The process according to the invention is characterized by the cobalt and, if present, the nickel having an average particle size of from 3 to 30 nm (nanometers) in the active catalyst.

Preference is given to the average particle size in the active catalyst being from 3 to 20 nm, more preferably from 3 to 15 nm, most preferably from 3 to 10 nm. The average particle size was determined by X-ray diffraction (Siemens D5000 diffractometer, TOPAS evaluation software). This catalyst used according to the invention has high activities owing to its large active surface area and small crystals and is notable for its long lifetime. To achieve the high activities, even small quantities of the catalytically active species are sufficient which allows inexpensive catalysts to be obtained.

The catalysts used according to the invention are prepared by a process comprising the following steps:
a) coprecipitation of cobalt and optionally, in addition, nickel and also at least one further doping metal from a solution comprising the corresponding salts of the metals mentioned onto a particulate support material,
b) subsequent drying and/or calcining,
c) optionally, molding, and
d) reduction.

a) Coprecipitation of Cobalt and, if Present, Nickel and also at Least One Further Doping Metal The catalysts used according to the invention are prepared by coprecipitation (mixed precipitation, coprecipitation) of their components onto a particulate support material. To this end, an aqueous salt solution comprising the catalyst components is generally admixed with stirring and heating at temperatures of from 20 to 100° C., preferably from 40 to 80° C., with an aqueous mineral base, preferably an alkali metal base, for example, sodium carbonate, sodium hydroxide, potassium carbonate, potassium hydroxide or ammonium carbonate, until the precipitation is substantially complete. Instead of a mineral base, an organic carboxylic acid which forms insoluble metal salts may also be used. An example of such an organic carboxylic acid is oxalic acid.

The type of metal salts used is generally not critical. Coprecipitation requires good water solubility of the salts used so that a criterion relating to the type of metal salts used is their good water solubility for preparing the relatively highly concentrated salt solutions. It is essential that the choice of the salts of the individual components only include salts of such anions which do not lead to problems, for example, owing to undesired precipitations or complex formation. Useful salts generally include the corresponding nitrates, acetates, formates, chlorides, sulfates and oxalates. The concentrations of the salt solutions are generally from 5 to 100%, preferably from 10 to 90%, more preferably from 25 to 75% of the maximum solubility of the salt or salts in water.

The coprecipitation may be carried out by any desired process known to those skilled in the art. In general, it is particularly advantageous to maintain constant conditions during the coprecipitation to obtain highly homogeneous precipitate. In one embodiment, the slightly basic solution of the mineral base at a desired pH of generally from 4 to 8, preferably from 5 to 7, more preferably from 5 to 6, is used as the initial charge and then the solutions of the appropriate metal salts (of cobalt, optionally of nickel and also of further doping metals), the slurried support material and further mineral base are added, preferably continuously, while keeping the pH constant. However, preference is given to using the support material at the desired pH of generally from 4 to 8, preferably from 5 to 7, more preferably from 5 to 6, as the initial charge and then adding the individual metal salt solutions of cobalt, optionally of nickel and of doping metals. Finally, it is also possible to use the support material together with the metal salts mentioned as the initial charge and then adding the mineral base until complete precipitation has occurred.

In general, the precipitation procedure is carried out at temperatures of from 20 to 100° C., preferably from 40 to 90° C., more preferably from 50 to 80° C. Depending on the metal salts used, the pH is from 4 to 7, preferably from 5 to 6.

In a preferred embodiment, the reaction mixture after precipitation is stirred for a certain time, in general from 10 to 90 min, preferably from 30 to 60 min, at the temperature mentioned, optionally while blowing in air. This further ages the mixture and thereby eases filtration. Finally, preference is given to raising the pH by adding further mineral base to a value of from 7 to 9, preferably from 7.5 to 8.5, in order to achieve virtually complete precipitation.

After the precipitation process, the precipitates obtained are filtered off and washed with water to remove all anions. The exact procedure is known to those skilled in the art.

b) Drying and/or Calcining

After the precipitates are filtered off and washed with water to remove all anions, they are dried and/or calcined. Preference is given to first drying and then calcining. The precipitates are generally dried at temperatures of from 70 to 150° C., preferably from 90 to 130° C. Drying is customarily carried out in an oven or in a spray dryer.

In order to decompose the carbonates, hydroxides or other compounds obtained depending on the anions used, the optionally dried solid is calcined. Calcining is effected at temperatures of generally from 250 to 600° C., preferably from 300 to 450° C. Examples of useful calcining devices include tray ovens and belt calciners. Both drying and calcining may be carried out using a temperature program which involves effecting the drying or calcining in a plurality of stages at differing temperatures. In general, drying takes from 2 to 24 hours, preferably from 6 to 15 hours. Calcining is generally effected over a period of from 1 to 24 hours, preferably from 2 to 10 hours, more preferably from 2 to 5 hours.

c) Optionally, Molding the Powder Obtained

In a preferred embodiment of the process according to the invention, the catalysts used according to the invention are used in a fixed bed process. Use in a fixed bed process requires shaping of the powder obtained after calcining. The shaping may be effected by processes known to those skilled in the art, for example by tableting or kneading and extrusion. To this end, shaping assistants such as Tylose®, Walocel®, potato starch, polyvinyl alcohol, lactic acid, polyethylene oxide and nitric acid are used.

d) Reduction

In the case of catalysts for use in fixed bed processes, shaping is followed by reduction of the catalyst precursors obtained. In a further embodiment of the process according to the invention, the catalysts are used as powders in a suspension process. In this case, no shaping takes place, and the reduction instead directly follows the calcining (step b).

Reduction is carried out using hydrogen at elevated temperatures of generally from 150 to 800° C., more preferably from 200 to 600° C. Preference is given to carrrying out the reduction of the cobalt catalysts used according to the invention in a plurality of stages. The first reduction stage is generally carried out at from 150 to 450° C., preferably from 175 to 400° C., more preferably from 200 to 350° C., for from 1 to 24 hours, preferably from 1.5 to 12 hours, more preferably from 2 to 6 hours. The second reduction stage takes place after heating to from 300 to 650° C., preferably from 350 to 550° C., more preferably from 400 to 500° C. This generally takes from 2 to 48 hours, preferably from 4 to 20 hours, more preferably from 6 to 15 hours. The second reduction stage may optionally be followed by a third reduction stage which is carried out in a range from 450 to 800° C., preferably from 475 to 700° C., more preferably from 500 to 600° C. over a period of from 0.5 to 10 hours, preferably from 0.5 to 8 hours, more preferably from 1 to 6 hours.

The reduction is generally carried out at a pressure of from 0.1 to 300 bar, preferably from 0.1 to 100 bar, more preferably from 1 to 10 bar. In a highly preferred embodiment, the reduction is carried out at atmospheric pressure.

A significant factor in obtaining the catalysts used according to the invention is the ratio of hydrogen used for the reduction to the catalyst quantity. Preference is therefore given to carrying out the reduction at a ratio of hydrogen to the catalyst quantity of >1 $Nm^3/h \times kg_{cat.}$, preferably of >2 $Nm^3/h \times kg_{cat.}$. Particular preference is given to employing a ratio of hydrogen quantity to catalyst quantity of from 1 to 10 $Nm^3/h \times kg_{cat.}$, and very particular preference to a ratio of from 1 to 5 $Nm^3/h \times kg_{cat.}$.

The water partial pressure in the hydrogen which on the industrial scale is generally circulated is generally ≦200 mbar, preferably from 0 to 200 mbar, more preferably from 0 to 100 mbar.

With the aid of this reduction step according to the invention, highly active catalysts are obtained which are notable for the particularly small cobalt and, if present, nickel crystal sizes and also a particularly high degree of reduction. The catalysts obtained in this manner are accordingly highly active and particularly suitable for the process according to the invention.

The catalysts obtained after reduction (d) are notable in that in general, at least 50%, preferably at least 65%, more preferably at least 70%, most preferably at least 75% of the cobalt and, if present, nickel in the catalyst are present in reduced form. This means that the catalysts used according to the invention comprise a particularly high fraction of active species and are therefore highly active even at low temperatures. The cobalt and, if present, the nickel in the catalysts used according to the invention are either cubic or hexagonal.

The doping metal present in the catalyst used according to the invention is generally selected from the group consisting of metals of groups IIIB, IVB, VB, VIB, VIIB, IIA, IIIA and VIA and the lanthanide group of the periodic table. Preference is given to using doping metals selected from the group consisting of metals of groups IIA, IIIB, IVB, IIIA, IVA and the lanthanide group. Particular preference is given to using doping metals selected from the group consisting of Ti, Zr, La, Y, Gd, Ce, Si, Al, Ga and Mg. With the aid of these doping metals, catalysts can be obtained which, as well as a high activity, have outstanding selectivities in the process according to the invention. It is possible for the catalysts used according to the invention to comprise at least one further doping metal selected from the group consisting of silver, gold and ruthenium, in addition to the doping metal selected from the groups mentioned.

The particulate support material may generally be any desired inert support material. For example, support materials may be selected from the group consisting of silicon dioxide, aluminum oxide, titanium dioxide, zirconium dioxide, silicon dioxide/aluminum oxide, aluminosilicates, calcium oxide, magnesium oxide, pumice and carbon and mixtures thereof. Preference is given to using support materials selected from the group consisting of silicon dioxide, aluminum oxide, titanium dioxide, zirconium dioxide, silicon dioxide/aluminum oxide, magnesium oxide and aluminosilicate. Very particular preference is given to using silicon dioxide and alumosilicates and also aluminum oxide and silicon dioxide/aluminum oxide and magnesium oxide as particulate support material.

In general, the doping metal is used in a quantity of from 1 to 90% by weight, preferably 5 to 70% by weight, more preferably from 10 to 50% by weight, based on the quantity of cobalt and, if present, nickel used. The mass ratio of cobalt and, if present, nickel to the sum of the support material and coprecipitated doping metal in oxide form is generally in the range from 20:80 to 80:20, preferably from 40:60 to 70:30. If nickel is present in the catalyst used according to the invention, the mass ratio of cobalt to nickel is in the range from 90:10 to 99.9:0.1, preferably from 80:20 to 99:1. The mass ratio of support material to coprecipitated doping metal in oxide form is generally in the range from 98:2 to 30:70, preferably from 90:10 to 50:50. The mass ratio of cobalt and, if present, nickel to silver, gold or ruthenium is generally in the range from 90:10 to 99.5:0.5.

The catalysts obtained in this way are outstandingly suitable for the hydrogenation according to the invention of nitrites to give primary amines under protective conditions.

The hydrogenation of nitrites may be carried out in different ways, and suitable process conditions are known to those skilled in the art. The hydrogenation may be carried out batchwise or continuously, although preference is given to a continuous method. Particular preference is given to carrying out the hydrogenation continuously in the liquid phase. The catalysts used in the process according to the invention are suitable in particular for continuous hydrogenation over a fixed bed or in suspension. When the hydrogenation is carried out over a fixed bed, either the trickle-bed method (downward flow through the reactor) or liquid phase method (upward flow through the reactor) may be employed. Useful reactors for hydrogenation over a solid bed include tube reactors. Particularly suitable embodiments of tube reactors are known to those skilled in the art.

When the hydrogenation is carried out in suspension, particularly useful reactors include stirred tanks, jet loop reactors or bubble columns.

However, it is also possible in principle to carry out the process according to the invention by batchwise operation. This involves adding the nitrile or a solution of the nitrile together with the catalyst into a high pressure autoclave, pressurizing with hydrogen and, if desired, ammonia and heating the reaction mixture. After the reaction has ended, the mixture is cooled, the catalyst removed and the reaction mixture fractionally distilled.

The hydrogen used in the hydrogenation is generally used in large stoichiometric excess. It may be recycled into the reaction as circuit gas. The hydrogen used is generally of technical purity. However, admixed inert gases, e.g. nitrogen, do not disturb the course of the reaction. The hydrogen pressure is generally from 0.5 to 30 MPa, preferably from 2.0 to 20 MPa, more preferably from 3.0 to 10 MPa.

The temperature in the process according to the invention is generally from 25 to 125° C., preferably from 25 to 100° C., more preferably from 50 to 100° C. Comparatively low temperatures during the process according to the invention enable the hydrogenation of thermally labile nitrites and also the achievement of defined isomeric ratios, for example in the case of isophoronediamine. Even at such low temperatures, the catalyst used according to the invention is very good owing to the small average particle size of cobalt and, if present, the nickel and the resulting large surface area.

It is possible to add organic solvents in the process according to the invention by hydrogenating nitrites. This is sensible when the nitrile is, for example, solid under normal conditions. Preferred organic solvents include aliphatic alcohols, e.g. methanol or ethanol, amides, e.g. N-methylpyrrolidone and dimethylformamide, ethers, e.g. dioxane or tetrahydrofuran and also esters. Particular preference is given to using tetrahydrofuran as solvent.

The catalyst hourly space velocity is generally in the range from 0.5 to 20 mol of nitrile/$l_{catalyst} \times h$, preferably from 2 to 10 mol of nitrile/$l_{catalyst} \times h$. When di- or polynitriles are hydrogenated and only a partial conversion is desired, the conversion and product ratio may be adjusted by changing the residence time.

It is possible to improve the selectivity toward primary amines by adding ammonia. However, outstanding selectivities are achieved even without adding ammonia. When ammonia is used, the quantity of ammonia is generally in the range from 6 to 60 mol of ammonia per mole of nitrile, preferably from 12 to 36 mol of ammonia per mole of nitrile.

In principle, all nitrites can be converted by the process according to the invention to primary amines. Useful nitrites include both mononitriles and dinitriles and also polynitriles having more than two nitrile groups. Preference is given to converting mononitriles or dinitriles into the corresponding amines. The process according to the invention is particularly suitable for the hydrogenation of Strecker nitrites which are obtainable by addition of formaldehyde and hydrocyanic acid to nucleophilic centers such as amines; of Michael nitrites which are accessible by addition of acrylonitrile to nucleophilic centers such as amines; of iminonitriles and also of dinitriles, in particular α, ω-dinitriles.

Particular preference is therefore given to using nitrites of the general formulae (I), (II), (III) or (IV) in the processes according to the invention:

$$R^1{}_{3-n}X\text{-}A\text{-}CN \qquad (I)$$

where the symbols are defined as follows:
X is O, S, N, P or C, preferably O, N or C
A is —$(CR^2R^3)_m$—, where $R^2$ and $R^3$ are each independently substituted or unsubstituted aryl, alkyl (branched or unbranched) or cycloalkyl radicals or hydrogen and m is from 0 to 8, preferably from 1 to 6, more preferably 1 or 2, or is a $C_2$- to $C_8$-alkylene chain, where the alkylene chain is interrupted by from 1 to 4, preferably from 1 to 3, more preferably 1 or 2 nonneighboring heteroatoms, or is phenylene, cyclohexylene, optionally substituted by radicals containing substituted or unsubstituted aryl, alkyl (branched or unbranched) or cycloalkyl radicals or by heteroatoms, preferably oxygen or nitrogen;

n is 2 (when X=O, S), 1 (when X=N, P) or 0 (when X=C);
$R^1$ is a substituted or unsubstituted aryl, alkyl (branched or unbranched) or cycloalkyl radical or hydrogen, although when m=0 or 1, the $R^1$ radicals may also be differing radicals selected from the $R^1$ group, or two $R^1$ radicals together with the heteroatom X (N, P, C) may form a cyclic radical which may be substituted in any desired manner and may be aromatic or cycloaliphatic;

$$NC\text{-}A\text{-}CN \qquad (II)$$

where A is as defined above;

(III)

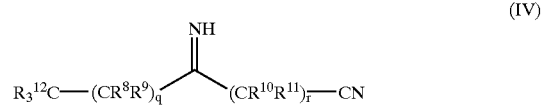
(IV)

where $R^4$, $R^5$, $R^6$, $R^7$, $R^8$, $R^9$, $R^{10}$, $R^{11}$ and $R^{12}$ are each independently substituted or unsubstituted aryl, alkyl (branched or unbranched) or cycloalkyl radicals or hydrogen, and
o, p, q, r are 0, 1, 2, 3, 4 or 5.

Particular preference is given to using nitrites of the general formulae (Ia) or (IIa):

$$R_{3-n}X\text{—}(CR^2R^3)_m\text{—}CN \qquad (Ia)$$

where
X is O or N,
m is 1 or 2, or $$NC\text{—}(CR^2R^3)_m\text{—}CN \qquad (IIa)$$

where
$R^2$ and $R^3$ are each independently alkyl radicals (branched or unbranched) or hydrogen and m is from 2 to 4.

Preference is also given to iminonitriles of the general formulae III or IV.

Nitriles used with preference in the process according to the invention and the amines produced from them are shown in the following table:

TABLE

| Amino compounds | Nitriles |
|---|---|
| H₂N⌒⌒NH₂ | H₂N⌒CN |
| H₂N⌒⌒N(H)⌒⌒NH₂ | NC⌒⌒N(H)⌒⌒CN |
| Me₂N⌒⌒NH₂ | Me₂N⌒⌒NH₂ |
| HO⌒⌒NH₂ | HO⌒CN |
| Ph-CH₂-NH₂ | Ph-CN |

TABLE-continued
| Amino compounds | Nitriles |
|---|---|
| 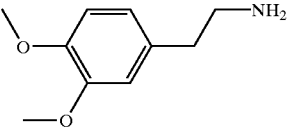 | 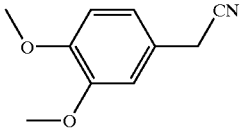 |
|  | 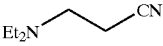 |
| 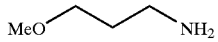 | 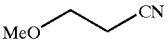 |
| 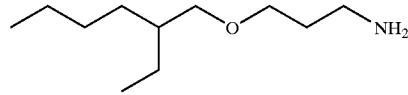 | 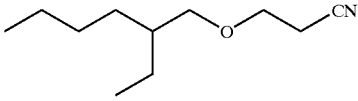 |
| 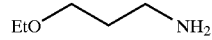 | 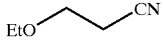 |
| 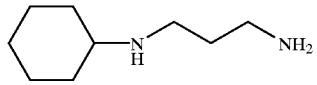 | 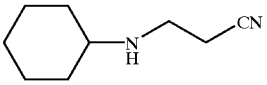 |
| 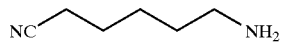 |  |
| 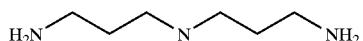 |  |
| 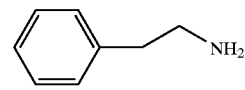 | 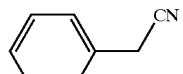 |
| 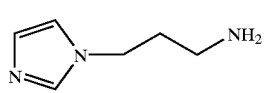 | 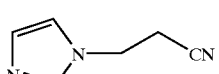 |
|  |  |
|  |  |
| 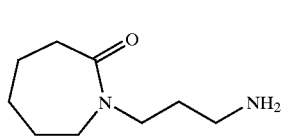 | 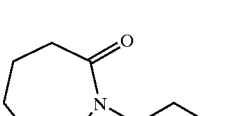 |
| 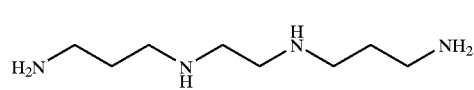 | 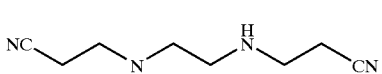 |
|  |  |
|  |  |
| 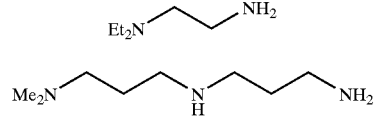 | 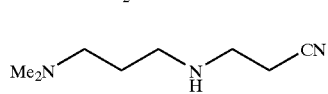 |
|  |  |

TABLE-continued

| Amino compounds | Nitriles |
|---|---|
| 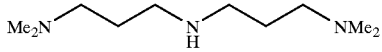 | 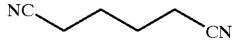 |
| 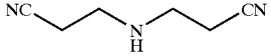 | 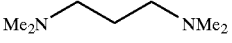 |
| 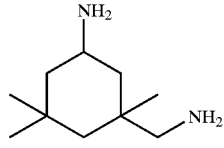 | 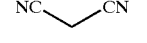 |
| 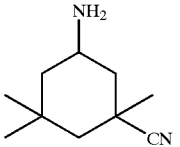 | 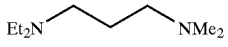 |
| 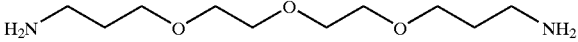 | 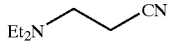 |
| 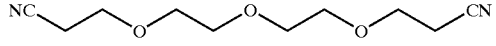 | 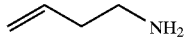 |
| 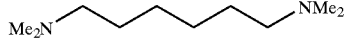 | 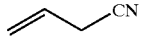 |

Very particular preference is given to using nitriles selected from the group consisting of adiponitriles, imidodiacetonitrile, biscyanoethylpiperazine, dimethylaminopropionitrile and isophoronenitrilimine.

The present invention also provides the use of a catalyst according to the invention in a process for preparing primary amines by hydrogenating nitriles. Preferred embodiments of the catalyst and also of the hydrogenation process and the suitable nitriles have already been discussed.

The invention is illustrated by the following examples:

EXAMPLES

Inventive Example 1
Preparation of a Fixed Bed Catalyst 163.2 g of an aluminosilicate powder (Siral 40 from Condea) are slurried with 2 l of demineralized water, finely dispersed using an Ultrathurax mill and introduced into a flask as an initial charge. 1222.0 g of $Co(NO_3)_2.6H_2O$, 25.5 g of $Ni(NO_3)_2.6H_2O$ und 625.0 g of 20% zirconium acetate solution are dissolved in 4 l of demineralized water. A 20% sodium carbonate solution (2885 g) is also prepared. Sodium carbonate solution and the metal salt solution are then simultaneously added dropwise at 90° C. with good stirring while maintaining a pH of 5.6. The precipitate is then stirred for an hour while passing air through at 90° C. Finally, the pH is raised to 7.5 by adding further sodium carbonate solution. After filtering off the precipitate with suction, the filter cake is washed with 100 l of demineralized water and dried overnight at 120° C. The mass obtained in this way is then finely ground in a kneader and then kneaded with 38.5 g of nitric acid, 390 g of demineralized water and 5 g of Tylose (from Clariant). When such a plastic mass was obtained, it was molded using an extruder at a molding pressure of 75 bar to give 3 mm extrudates. These were dried overnight at 150° C. and then calcined at 400° C. for 4 h. 25 g of these extrudates were reduced using 45 l/h (STP) of hydrogen and 5 l/h (STP) of nitrogen according to the following temperature program: heat within one hour at 300° C., maintain this temperature for 4 hours, heat to 450° C. within one hour, maintain this temperature for 10 hours, heat within one hour to 540° C., maintain this temperature for 2 hours and allow to cool under nitrogen.

Analysis of the reduced extrudates by X-ray diffraction showed that more than 80% of the cobalt is present in reduced form. The average Co crystal size is 8 nm. The Co content is 49% by weight, the Ni content 1% by weight of the total mass.

Inventive Example 2
Preparation of a Fixed Bed Catalyst 125.0 g of a silicon dioxide powder (D11-10-40 from BASF) are slurried with 2 l of demineralized water, finely dispersed using an Ultrathurax mill and introduced into a flask as an initial charge. 1222.0 g of $Co(NO_3)_2.6H_2O$, 25.5 g of $Ni(NO_3)_2.6H_2O$ und 625.0 g of 20% zirconium acetate solution are dissolved in 4 l of demineralized water. A 20% sodium carbonate solution (3134 g) is also prepared. Sodium carbonate solution and the metal salt solution are then simultaneously added dropwise at 90° C. with good stirring while maintaining a pH of 5.6. The precipitate is then stirred for an hour while passing air through at 90° C. Finally, the pH is raised to 7.5 by adding further sodium carbonate solution. After filtering off the precipitate with suction, the filter cake is washed with 100 l of demineralized water and half of the filter cake is dried overnight at 120° C., and the other half overnight at 150° C. The mass obtained in this way is then finely ground in a kneader and then kneaded with 30 g of demineralized water. When such a plastic mass was obtained, it was molded using an extruder press at a molding pressure of 70 bar to give 3 mm extrudates. These were dried at 120° C. for 16 hours and then calcined at 400° C. for 4 h. 100 g of these extrudates were reduced using 180 l/h (STP) of hydrogen and 20 l/h (STP) of nitrogen according to the following temperature program: heat within one hour at 300° C., maintain this temperature for 4 hours, heat to 450° C. within one hour, maintain this temperature for 10 hours, heat within one hour to 540° C., maintain this temperature for 2 hours and allow to cool under nitrogen.

A portion of the extrudates was analyzed, but the largest portion of the extrudates was passivated by passing an air/nitrogen mixture over it at 50° C.

Analysis of the reduced extrudates by X-ray diffraction showed that more than 80% of the cobalt is present in reduced form. The average Co crystal size is 8 nm. The Co content is 49% by weight, the Ni content 1% by weight of the total mass.

Inventive Example 3
Hydrogenation of Adiponitrile in the Fixed Bed in the Presence of the Catalyst from Inventive Example 1

100 ml of the catalyst from Inventive Example 1 (=89.1 g) were installed into a continuously operated pressure apparatus (tube reactor, straight pass, equipped with an internal thermocouple sheath). The reactor was then inertized using nitrogen. The catalyst was then reduced by passing 250 l/h (STP) of hydrogen over it at 70 bar according to the following temperature program: heat within five hours to 300° C., maintain this temperature for 4 hours, heat within three hours to 450° C., maintain this temperature for 16 hours, heat within one hour to 500° C., maintain this temperature for 3 hours and allow to cool under hydrogen. After cooling the plant, the reaction was started using 100 l/h (STP) of hydrogen, 150 g/h of ammonia and 50 g/h of adiponitrile at 70 bar and an entrance temperature of 65° C. The feed loading is accordingly 1.12 g of adiponitrile per g of active mass (Co+Ni). After operating for 34 h, the conversion of adiponitrile was 93.4%.

Inventive Example 4
Hydrogenation of Adiponitrile in a Fixed Bed in the Presence of the Catalyst from Inventive Example 2

100 ml of the catalyst from Inventive Example 2 (=86.3 g) were installed in reduced/passivated form into a continuously operated pressure apparatus (tube reactor, straight pass, equipped with an internal thermocouple sheath). The reactor was then inertized using nitrogen. The passivated catalyst was then activated by passing 250 l/h (STP) of hydrogen over it at 70 bar according to the following temperature program: heat to 320° C. within six hours, maintain this temperature for 40 hours, heat to 450° C. within two hours, maintain this temperature for 6 hours and allow to cool under nitrogen. After cooling the plant, the reaction was started using 100 l/h (STP) of hydrogen, 150 g/h of ammonia and 50 g/h of adiponitrile at 70 bar and an entrance temperature of 65° C. The feed loading is accordingly 1.16 g of adiponitrile per g of active mass (Co+Ni). After operating for 22 h, the conversion of adiponitrile was 88.1%.

Comparative Example 1
Preparation of a Raney Fixed Bed Catalyst 90 ml of water were added in portions to 900 g of a powdered alloy consisting of 49.14% by weight of aluminum, 49.2% by weight of cobalt, 1.11% by weight of chromium, 0.54% by weight of nickel and 0.01% by weight of iron (Essex Metallurgical Co. Ltd.), 80 g of polyvinyl alcohol (molecular weight 9000–18 000 g/mol) and 8 g of Tylose H2000 P (Clariant) in a kneader. After a kneading time of three hours, the plastic mass was molded at a molding pressure of 14 MPa in an extruder to give 3 mm extrudates. The extrudates were dried for 16 h under air, then dried at 120° C. for 16 h and then calcined at 450° C. for 1 h, 750° C. for 1 h and 900° C. for 2 h. The extrudates were then comminuted in a jaw crusher to give spall of the particle size fraction 1.5–4 mm. 400 g of these extrudates were added at 60° C. to 3000 g of a 20% sodium hydroxide solution. Once hydrogen formation had abated, the mixture was heated to 90° C. and this temperature was maintained for 3 h. The activated catalyst was washed with sodium hydroxide and with water and was then ready for installation into the reactor. The cobalt content was 45% by weight, the nickel content 0.5% by weight.

Comparative Example 2
Hydrogenation of Adiponitrile in the Fixed Bed in the Presence of the Catalyst from Comparative Example 1

200 ml of the catalyst from Comparative Example 1 (=236 g) were installed into a continuously operated pressure apparatus (tube reactor, straight pass, equipped with an internal thermocouple sheath). Afterwards, the reactor was inertized using nitrogen. The reactor was then purged for five hours using 500 g/h of ethanol. The reaction was then started using 200 l/h (STP) of hydrogen, 300 g/h of ammonia and 100 g/h of adiponitrile at 70 bar and an entrance temperature of 65° C. The feed loading is accordingly 0.93 g of adiponitrile per g of active mass (Co+Ni). After an operating time of 21 h, the conversion of adiponitrile was 63.0%.

This comparative example shows that the precipitated Co catalysts of the invention have a higher activity that the Raney catalysts. These precipitated catalysts are also not accompanied by the handling disadvantages of the Raney catalysts.

Inventive Example 5
Preparation of a Suspension Catalyst 60.7 g of an aluminosilicate powder (Siral 40 from Condea) are slurried with 0.5 l of demineralized water, finely dispersed using an Ultrathurax mill and introduced into a flask as an initial charge. 222.4 g of $Co(NO_3)_2.6H_2O$, 5.1 g of $Ni(NO_3)_2.6H_2O$ und 14.5 g of $Y(NO_3)_3.5H_2O$ are dissolved in 0.5 l of demineralized water. A 20% sodium carbonate solution (851 g) is also prepared. Sodium carbonate solution and the metal salt solution are then simultaneously added dropwise at 65° C. with good stirring while maintaining a pH of 5.6. The precipitate is then stirred for an hour while passing air through at 65° C. Finally, the pH is raised to 7.5 by adding further sodium carbonate solution. After filtering off the precipitate with suction, the filter cake is washed with 20 l of demineralized water, dried overnight at 120° C. and calcined for 4 h at 400° C. 25 g of this powder were reduced using 45 l/h (STP) of hydrogen and 5 l/h (STP) of nitrogen according to the following temperature program: heat to 300° C. within one hour, maintain this temperature for 4 hours, heat to 470° C. within one hour, maintain this temperature for 9 hours, heat to 600° C. within one hour, maintain this temperature for 3 hours and allow to cool under nitrogen.

Analysis of the reduced extrudates by X-ray diffraction showed that more than 70% of the cobalt is present in reduced form. The average Co crystal size is 6.5 nm. The Co content is 49% by weight, the Ni content 1% by weight of the total mass.

Inventive Example 6
Hydrogenation of Dimethylaminopropionitrile in the Presence of the Catalyst from Inventive Example 5

6 g of the catalyst from Inventive Example 5 with 57.3 g of dimethylaminopropionitrile were installed into a 270 ml pressure autoclave equipped with a gas dispersion stirrer. The autoclave was then inertized using nitrogen. 50 g of ammonia were then injected and the reactor heated to 80° C. At this temperature, the reactor was pressurized to 80 bar by injecting hydrogen. After a reaction time of 125 min, the reactor was cooled to room temperature, depressurized and the ammonia-free reactor effluent was analyzed by means of gas chromatography. The conversion of dimethylaminopropionitrile (DMAPN) was 100%, the selectivity toward dimethylaminopropylamine (DMAPA) was 98.4%.

Comparative Example 3
Preparation of an Unsupported Catalyst According to Example 1 of WO 97/10052

A stirred flask is initially charged with a solution of 42.4 g of $Na_2CO_3$ in 200 ml of demineralized water and heated to 80° C. To this solution, a second solution consisting of 200 ml of demineralized water, 66.14 g of $Co(NO_3)_2.6H_2O$ and 30.62 g of $Cr(NO_3)_3.9H_2O$ is added dropwise within a few minutes with stirring. The molar ratio of Co:Cr is 3:1. After the dropwise addition, stirring is continued at 80° C. for 20 min, then the precipitate is filtered off and washed with 1.5 l of hot water at 80° C. The washed filter cake is dried at 120° C. for 12 h and then calcined at 300° C. for 3 h to decompose the carbonate. The oxidic catalyst is then reduced with hydrogen at 350° C. for 29 h.

Comparative Example 4
Hydrogenation of Dimethylaminopropionitrile in the Presence of the Catalyst from Comparative Example 3

6 g of the catalyst from Comparative Example 3 with 57.3 g of dimethylaminopropionitrile were installed into a 270 ml pressure autoclave equipped with a gas dispersion stirrer. The autoclave was then inertized using nitrogen. 50 g of ammonia were then injected and the reactor heated to 80° C. At this temperature, the reactor was pressurized to 80 bar by injecting hydrogen. After a reaction time of 333 min, the reactor was cooled to room temperature, depressurized and the ammonia-free reactor effluent was analyzed by means of gas chromatography. The conversion of DMAPN was 22.6%, the selectivity toward DMAPA was 83.6%.

This comparative example makes clear that an unsupported catalyst prepared according to Example 1 of WO 97/10052 is inferior to the catalysts according to the invention in respect of activity and selectivity.

We claim:

1. A process for preparing primary amines by hydrogenating nitriles in the presence of a catalyst comprising cobalt and optionally, in addition, nickel and also at least one further doping metal on a particulate support material, the cobalt and, if present, the nickel having an average particle size of from 3 to 30 nm in the active catalyst.

2. A process as claimed in claim 1, wherein the catalyst is prepared by the following steps:
   a) coprecipitation of cobalt and optionally, in addition, nickel and also at least one further doping metal from a solution comprising the corresponding salts of the metals mentioned onto a particulate support material,
   b) subsequent drying and/or calcining,
   c) optionally, molding; and
   d) reduction.

3. A process as claimed in claim 1, wherein the at least one further doping metal is selected from the group consisting of metals of groups IIIB, IVB, VB, VIB, VIIB, IIA, IIIA and VIA and the lanthanide group of the periodic table.

4. A process as claimed in claim 3, wherein the at least one doping metal is selected from the group consisting of Ti, Zr, La, Y, Gd, Ce, Si, Al, Ga and Mg.

5. A process as claimed in claim 1, wherein the catalyst comprises at least one further doping metal selected from the group consisting of silver, gold and ruthenium.

6. A process as claimed in claim 1, wherein the particulate support material is selected from the group consisting of silicon dioxide, aluminum oxide, titanium dioxide, zirconium dioxide, silicon dioxide/aluminum oxide, aluminosilicates and magnesium oxide.

7. A process as claimed in claim 1, wherein the mass ratio of cobalt and, if present, nickel to the sum of support material and coprecipitated doping metal in oxide form is in the range from 20:80 to 80:20 or the mass ratio of support material to concomitantly precipitated doping metal in oxide form is in the range from 98:2 to 30:70.

8. A process as claimed in claim 1, wherein at least 65% of the cobalt and, if present, the nickel are present in reduced form.

9. A process as claimed in claim 2, wherein the reduction in step d) is carried out at a ratio of hydrogen quantity to catalyst quantity of >1 $Nm^3/h \times kg_{cat}$.

10. A process as claimed in claim 1, wherein the hydrogenation temperature is from 25 to 125° C.

11. A process for preparing primary amines by hydrogenating nitriles in the presence of a catalyst comprising cobalt and optionally, in addition, nickel and also at least one further doping metal on a particulate support material, the cobalt and, if present, the nickel having an average particle size of from 3 to 30 nm in the active catalyst, wherein nitriles of the following general formulae (I), (II), (III) or (IV) are used:

where the symbols are defined as follows:
X is O, S, N, P or C,
A is —$(CR^2R^3)_m$—, where $R^2$ and $R^3$ are each independently substituted or unsubstituted aryl, alkyl (branched or unbranched) or cycloalkyl radicals or hydrogen and m is from 0 to 8, or
is a $C_2$- to $C_8$-alkylene chain, where the alkylene chain is interrupted by from 1 to 4 nonneighboring heteroatoms, or
is phenylene, cyclohexylene, optionally substituted by radicals containing substituted or unsubstituted aryl, alkyl (branched or unbranched) or cycloalkyl radicals or by heteroatoms;
n is 2 (when X=O, S), 1 (when X=N, P) or 0 (when X=C);
$R^1$ is a substituted or unsubstituted aryl, alkyl (branched or unbranched) or cycloalkyl radical or hydrogen, although when m=0 or 1, the $R^1$ radicals may also be differing radicals selected from the $R^1$ group, or two $R^1$ radicals together with the heteroatom X (N, P, C) may form a cyclic radical which may be substituted in any desired manner and may be aromatic or cycloaliphatic;

where A is as defined above;

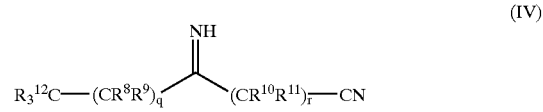

where $R^4$, $R^5$, $R^6$, $R^7$, $R^8$, $R^9$, $R^{10}$, $R^{11}$ and $R^{12}$ are each independently substituted or unsubstituted aryl, alkyl (branched or unbranched) or cycloalkyl radicals or hydrogen, and
o, p, q, r are 0, 1, 2, 3, 4 or 5.

12. A process as claimed in claim 11, wherein the catalyst is prepared by the following steps:
   a) coprecipitation of cobalt and optionally, in addition, nickel and also at least one further doping metal from a solution comprising the corresponding salts of the metals mentioned onto a particulate support material,
   b) subsequent drying and/or calcining,
   c) optionally, molding; and
   d) reduction.

13. A process as claimed in claim 11, wherein the at least one further doping metal is selected from the group consisting of metals of groups IIIB, IVB, VB, VIB, VIIB, IIA, IIIA and VIA and the lanthanide group of the periodic table.

14. A process as claimed in claim 13, wherein the at least one doping metal is selected from the group consisting of Ti, Zr, La, Y, Gd, Ce, Si, Al, Ga and Mg.

15. A process as claimed in claim 11, wherein the catalyst comprises at least one further doping metal selected from the group consisting of silver, gold and ruthenium.

16. A process as claimed in claim 11, wherein the particulate support material is selected from the group consisting of silicon dioxide, aluminum oxide, titanium dioxide, zirconium dioxide, silicon dioxide/aluminum oxide, aluminosilicates and magnesium oxide.

17. A process as claimed in claim 11, wherein the mass ratio of cobalt and, if present, nickel to the sum of support material and coprecipitated doping metal in oxide form is in the range from 20:80 to 80:20 or the mass ratio of support material to concomitantly precipitated doping metal in oxide form is in the range from 98:2 to 30:70.

18. A process as claimed in claim 11, wherein at least 65% of the cobalt and, if present, the nickel are present in reduced form.

19. A process as claimed in claim 12, wherein the reduction in step d) is carried out at a ratio of hydrogen quantity to catalyst quantity of >1 $Nm^3/h \times kg_{cat}$.

20. A process as claimed in claim 11, wherein the hydrogenation temperature is from 25 to 125° C.

21. A process as claimed in claim 11, wherein the following nitriles are used:

$$R_{3-n}X\text{---}(CR^2R^3)_m\text{---}CN \tag{Ia}$$

where
   X is O or N,
   m is 1 or 2; or $$NC\text{---}(CR^2R^3)_m\text{---}CN \tag{IIa}$$

where $R^2$ and $R^3$ are each independently alkyl radicals (branched or unbranched) or hydrogen and m is from 2 to 4; or
iminonitriles of the general formulae III or IV.

22. A process as claimed in claim 21, wherein the nitriles used are selected from the group consisting of adiponitrile, imidodiacetonitrile, biscyanoethylpiperazine, dimethylaminopropionitrile and isophoronenitrilimine.

23. A process as claimed in claim 11, wherein the mass ratio of cobalt and, if present, nickel to the sum of support material and coprecipitated doping metal in oxide form, is in the range from 20:80 to 80:20 or the mass ratio of support material to concomitantly precipitated doping metal in oxide form is in the range from 98:2 to 30:70.

24. A process as claimed in claim 21, wherein the catalyst is prepared by the following steps:
   a) coprecipitation of cobalt and optionally, in addition, nickel and also at least one further doping metal from a solution comprising the corresponding salts of the metals mentioned onto a particulate support material,
   b) subsequent drying and/or calcining,
   c) optionally, molding; and
   d) reduction.

25. A process as claimed in claim 11, wherein
   A is —$(CR^2R^3)_m$—; where $R^2$ and $R^3$ are each independently substituted or unsubstituted aryl, alkyl (branched or unbranched) or cycloalkyl radicals or hydrogen and m is from 0 to 8, or
   is a $C_2$- to $C_8$-alkylene chain, where the alkylene chain is interrupted by from 1 to 4 nonneighboring heteroatoms, or
   is phenylene, cyclohexylene, optionally substituted by radicals containing substituted or unsubstituted aryl, alkyl (branched or unbranched) or cycloalkyl radicals or by oxygen or nitrogen.

* * * * *